US009402549B2

(12) United States Patent
Wang et al.

(10) Patent No.: US 9,402,549 B2
(45) Date of Patent: Aug. 2, 2016

(54) METHODS AND APPARATUS TO ESTIMATE VENTRICULAR VOLUMES

(71) Applicant: General Electric Company, Schenectady, NY (US)

(72) Inventors: Zhijie Wang, Barrington, IL (US); Shuo Li, London (CA); Ali Islam, Barrington, IL (US); Aashish Goela, Barrington, IL (US)

(73) Assignee: General Electric Company, Schenectady, NY (US)

( * ) Notice: Subject to any disclaimer, the term of this patent is extended or adjusted under 35 U.S.C. 154(b) by 261 days.

(21) Appl. No.: 14/092,453

(22) Filed: Nov. 27, 2013

(65) Prior Publication Data

US 2015/0146950 A1    May 28, 2015

(51) Int. Cl.
*G06K 9/00* (2006.01)
*A61B 5/02* (2006.01)
*A61B 5/055* (2006.01)
*G06T 7/00* (2006.01)
*A61B 5/107* (2006.01)
*A61B 5/00* (2006.01)

(52) U.S. Cl.
CPC ............ *A61B 5/02028* (2013.01); *A61B 5/055* (2013.01); *A61B 5/1073* (2013.01); *A61B 5/1075* (2013.01); *G06T 7/0014* (2013.01); *A61B 5/72* (2013.01); *G06T 2207/10088* (2013.01); *G06T 2207/20104* (2013.01); *G06T 2207/30048* (2013.01)

(58) Field of Classification Search
CPC .. A61B 5/02028; A61B 5/055; A61B 5/1073; A61B 5/1075; A61B 5/72; G06T 7/0014; G06T 2207/10088; G06T 2207/20104; G06T 2207/30048
See application file for complete search history.

(56) References Cited

U.S. PATENT DOCUMENTS

| | | |
|---|---|---|
| 8,235,910 B2 | 8/2012 | Parlikar et al. |
| 2002/0193689 A1 | 12/2002 | Bernstein et al. |
| 2003/0053667 A1 | 3/2003 | Paragios et al. |
| 2003/0069494 A1 | 4/2003 | Jolly |
| 2003/0199779 A1 | 10/2003 | Muhlenberg et al. |
| 2004/0024329 A1 | 2/2004 | Jansen et al. |
| 2004/0082846 A1 | 4/2004 | Johnson et al. |
| 2005/0020891 A1 | 1/2005 | Rubinstein et al. |
| 2005/0031600 A1 | 2/2005 | Mickle et al. |
| 2005/0059876 A1 | 3/2005 | Krishnan et al. |
| 2005/0238215 A1 | 10/2005 | Jolly et al. |
| 2005/0288598 A1 | 12/2005 | Lavi et al. |
| 2007/0016019 A1 | 1/2007 | Salgo |

(Continued)

OTHER PUBLICATIONS

Wang et al., "Direct Estimation of Cardiac Bi-ventricular Volumes with an Adapted Bayesian Formulation," IEEE Transactions on Biomedical Engineering, vol. 61, No. 4, Apr. 2014, 9 pages.
Qazi et al., "Automated Heart Wall Motion Abnormaility Detection From Ultrasound Images using Bayesian Networks," International Joint Conferences on Artificial Intelligence, 2007, 7 pages.
Petitjean et al., "A Review of Segmentation Methods in Short Axis Cardiac MR Images," Medical Image Analysis, Jan. 1, 2011, 47 pages.

(Continued)

*Primary Examiner* — Shefali Goradia
(74) *Attorney, Agent, or Firm* — Hanley, Flight and Zimmerman, LLC (57) ABSTRACT

Methods and apparatus to estimate ventricular volumes are disclosed. An example computer-implemented method includes preparing a sample set using a prior probability model for a left ventricle and a right ventricle and using a likelihood function to assign a weight to each sample within the sample set. The example method also includes, based on the weighted sample set, determining an area of the right ventricle and the left ventricle.

22 Claims, 11 Drawing Sheets

(56) References Cited

U.S. PATENT DOCUMENTS

| | | | |
|---|---|---|---|
| 2007/0032749 A1 | 2/2007 | Overall et al. | |
| 2007/0055170 A1 | 3/2007 | Lippert et al. | |
| 2007/0083118 A1 | 4/2007 | Dala-Krishna | |
| 2007/0149884 A1 | 6/2007 | Roteliuk et al. | |
| 2007/0197921 A1 | 8/2007 | Cohen et al. | |
| 2007/0203403 A1 | 8/2007 | Rubinstein et al. | |
| 2008/0181479 A1* | 7/2008 | Yang | A61B 5/0456 382/131 |
| 2008/0200784 A1 | 8/2008 | Cheng | |
| 2009/0093707 A1 | 4/2009 | Maier | |
| 2009/0161926 A1 | 6/2009 | Florin et al. | |
| 2009/0290777 A1 | 11/2009 | Sun et al. | |
| 2010/0040270 A1 | 2/2010 | Li et al. | |
| 2010/0168554 A1 | 7/2010 | Sorensen | |
| 2010/0179421 A1 | 7/2010 | Tupin | |
| 2010/0210945 A1 | 8/2010 | Zhang | |
| 2010/0303328 A1 | 12/2010 | Ciofolo et al. | |
| 2011/0206247 A1 | 8/2011 | Dachille et al. | |
| 2011/0262018 A1 | 10/2011 | Kumar et al. | |
| 2011/0301466 A1 | 12/2011 | Wang et al. | |
| 2012/0022336 A1* | 1/2012 | Teixeira | A61B 5/0205 600/300 |
| 2012/0121152 A1 | 5/2012 | Lu et al. | |
| 2012/0203090 A1 | 8/2012 | Min | |

OTHER PUBLICATIONS

Frangi et al., "Three-Dimensional Modeling for Functional Analysis of Cardiac Images: A Review," IEEE Transactions on Medical Imaging, vol. 20, No. 1, Jan. 2001, 24 pages.

Corsi et al., "Improved Quantification of Left Ventricular Volumes and Mass Based on Endocardial and Epicardial Surface Detection from Cardiac MR Images using Level Set Models," Journal of Cardiovascular Magnetic Resonance, 2005, 8 pages.

Mariam Afshin, "Automatic Assessment of Cardiac Left Ventricular Function via Magnetic Resonance Images," Doctoral Thesis, The School of Graduate and Postdoctoral Studies, Western University, 2012, 158 pages.

Lynch et al., "Segmentation of the Left Ventricle of the Heart in 3-D+t MRI Data Using an Optimized Nonrigid Temporal Model," IEEE Transactions on Medical Imaging, vol. 27, No. 2, Feb. 2008, pp. 195-203, 9 pages.

Rahman et al., "Combining Short-axis and Long-axis Cardiac MR Images by Applying a Super-resolution Reconstruction Algorithm," Medical Imaging 2010: Image Processing, Mar. 12, 2010, 12 pages.

Montenegro Da Silva, "Toward a Fully Automatic Left Ventricle Segmentation using Cine-MR Images," Masters Thesis, Universidade Tecnica de Lisboa, Oct. 2008, 86 pages.

* cited by examiner

METHODS AND APPARATUS TO ESTIMATE VENTRICULAR VOLUMES

FIELD OF THE DISCLOSURE

This disclosure relates generally to estimating ventricular volumes, and, more particularly, to methods and apparatus to estimate ventricular volumes.

BACKGROUND

Cardiovascular diseases are the leading cause of death in western countries. To diagnosis and treat cardiovascular diseases, the cardiac functions of the left ventricle and the right ventricle may be analyzed.

BRIEF DESCRIPTION OF THE DRAWINGS

The figures are not to scale. Wherever possible, the same reference numbers will be used throughout the drawing(s) and accompanying written description to refer to the same or like parts.

DETAILED DESCRIPTION

Cardiovascular diseases are a leading cause of death in western countries. Determined ventricular volumes can be used to globally assess cardiac functions. To diagnose and treat these diseases, both the left and right ventricles are analyzed using ventricular volumes, ejection fraction (EF) and/or stroke volumes, etc. Some of these known estimating methods are limited to estimating the volume of the left ventricle using segmentation, which is computationally expensive, slow and tedious. In contrast to some known methods, the examples disclosed herein estimate the volume of the left ventricle and the right ventricle jointly and/or substantially simultaneously using an example segmentation-free method that uses an example adapted Bayesian formulation. Specifically, in some examples, the left and right ventricle volumes are determined using the Bayesian formulation that includes an example likelihood model and an example prior probability model where the likelihood model uses multiple appearance features and the prior probability model correlates the areas and/or other features between the left ventricular cavity and the right ventricular cavity. Thus, using the examples disclosed herein, a direct, efficient and accurate assessment of global cardiac functions can be determined.

In some of the illustrated examples, based on an initial input of manually or automatically identifying attachment locations between a right ventricle and a left ventricular septal wall, the bi-ventricular volumes can be estimated without manual and automatic contouring. The cavity areas (e.g., short-axis view cavity areas) can be estimated with a Bayesian framework and the bi-ventricular volume can be estimated by integrating the cavity areas along a sagittal direction. Thus, the bi-ventricular volumes can be estimated without manual and automatic contouring. Using the estimated bi-ventricular volumes, the cardiac functional parameters for both the left and right ventricles can be determined efficiently and simultaneously. In some examples, the estimated volumes can be used to estimate functional parameters of the heart such as end-systolic volume, end-diastolic volume, ejection fraction, cardiac output, peak ejection rate, filling rate, etc.

Figure 1:
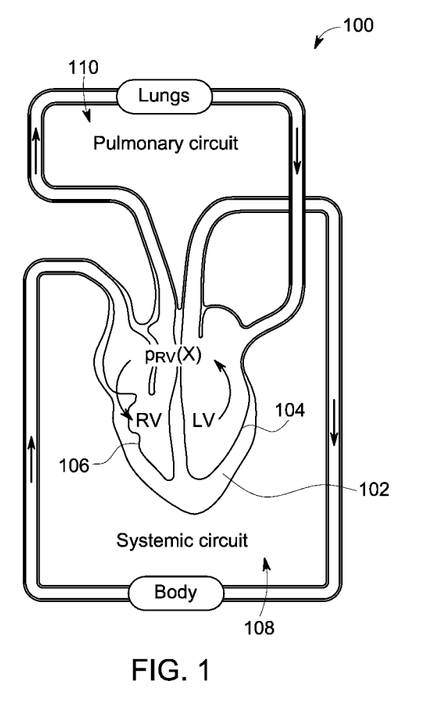
FIG. 1 illustrates a schematic illustration of a closed circulation heart system.

FIG. 1 illustrates a schematic illustration of a closed circulation heart system 100 including a heart 102 having a left ventricle 104, a right ventricle 106, a systemic circuit 108 and a pulmonary circuit 110. Because the left ventricle 104 and the right ventricle 106 both belong to the closed circulation heart system 100 and are physically connected, the left and right ventricles 104, 106 share the same motion pattern of cyclically expanding during a diastolic period and contracting during a systolic period. Thus, the volumes of the left and right ventricles 104, 106 similarly change as the heart 102 transitions through the different phases.

Figure 2:
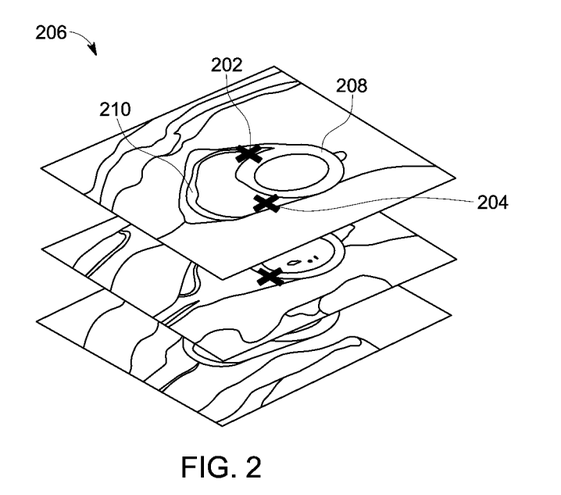
FIG. 2 illustrates a frame of magnetic resonance imaging (MRI) sequence showing an initial input, identification and/or selection of first and second landmarks in accordance with the teachings of this disclosure.

FIG. 2 illustrates a frame 200 of an MRI sequence 200 showing an initial input, identification and/or selection of first and second landmarks 202, 204 on a frame 200 of the MRI sequence.

Figure 3:
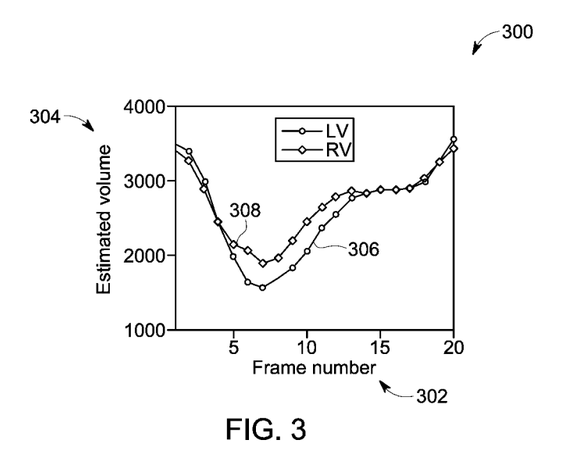
FIG. 3 shows a graph of estimated volumes of a left ventricle and a right ventricle over a cardiac cycle in accordance with the teaching of this disclosure.

The first landmark 202 corresponds to a first attachment point between a left ventricular septal wall 208 and a right ventricular wall 210 and the second landmark 204 corresponds to a second attachment point between the right ventricular wall 210 and the left ventricular septal wall 208. In the illustrate examples, the landmarks 202, 204 are used to automatically estimate the bi-ventricular volumes throughout a cardiac cycle in real time, the results of which are shown in FIG. 3. FIG. 3 shows a graph 300 of the estimated volumes of the left ventricle and the right ventricle over a cardiac cycle where the x-axis 302 corresponds to a frame number, the y-axis 304 corresponds to an estimated volume, a first line 306 is associated with the left ventricle and a second line 308 is associated with the right ventricle.

Figure 4:
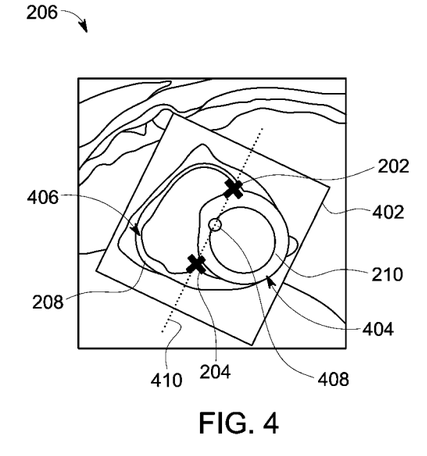
FIG. 4 shows a frame in which a region of interest (ROI) has been selected that encloses both a left ventricle and a right ventricle in accordance with the teachings of this disclosure.

FIG. 4 shows the frame 200 in which a region of interest (ROI) 402 has been selected that encloses both a left ventricle 404 and a right ventricle 406. In the illustrated examples, the landmarks and/or the user selections 202, 204 enable consistency to be maintained between different potential regions of interest (ROIs) and/or between different frames and/or patients. Specifically, in the illustrated examples, the anatomical significance of the landmarks 202, 204 enables the ROI selections to be consistent and for the final estimated results to be robust to intra-user variability and/or inter-user variability.

Using the ROI selection 402 of FIG. 4, a central point 408 between the landmarks 202, 204 can be identified in the center of the squared ROI selection 402. In the illustrated examples, the scale of the central point 408 is twice as large as a distance between the landmarks 202, 204. In some examples, a central line 410 that couples and/or links the landmarks 202, 204 can be used to orient the ROI selection 402 as shown in FIG. 5.

Figure 5:
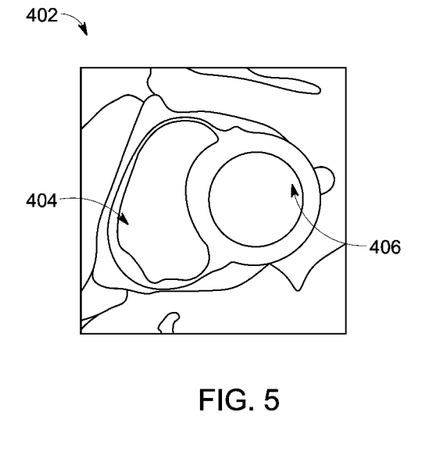
FIG. 5 shows a more detailed view of the region of interest of FIG. 4.

FIG. 5 illustrates the ROI selection 402 having been rotated such that the central line 410 is vertical relative to the bottom of the ROI selection 402 and the central line 410 separates the left ventricle 404 and the right ventricle 406. In the illustrated example of FIG. 5, the ROI selection 402 has been rescaled to 40×40 pixels. Using the illustrated examples of FIGS. 4 and 5, a single ROI selection can be used to analyze both the left ventricle 404 and the right ventricle 406. Using the illustrated examples of FIGS. 4 and 5 and correlation information of an example probability model, both the left ventricle 404 and the right ventricle 406 can be jointly examined within the ROI selection 402.

In the illustrated examples, the cavity areas (Ai) of the left ventricle 404 and the right ventricle 406, respectively, are determined using an example Bayesian formulation. The example Bayesian formulation may be used and/or adapted to incorporate different models and/or constraints related to appearance, motion, etc. In the example Bayesian framework, statistical pattern recognition includes estimating a posterior probability density of an object parameterized by X given a prior, p(X), and an observation, (Z). In some examples, Equation 1 represents the posterior probability of X given the observation, Z, where p(X|Z) is a likelihood function modeling a probability of observing Z given an object state, X, and p(X) is a prior probability of the object state.

$$p(X|Z) \propto p(Z|X)p(X) \qquad \text{Equation 1}$$

Equation 2 is a modified example Bayesian formulation used to estimate bi-ventricle volumes and/or areas based at least in part on physical aspects of the heart and/or the left and right ventricles. Referring to Equation 2, the LV corresponds to the left ventricle, RV corresponds to the right ventricle and p(Z|X) corresponds to an example multi-feature likelihood function. In some examples, the connections are determined by $P_{RV}(X)$ (e.g., an example right ventricle probability model; an example area correlation prior probability model), which is modeled as a function of $P_{LV}(X|Z)$ (e.g., an example left ventricular posterior probability) and uses the estimated left ventricle area as a prior based on a correlation between the left ventricle and the right ventricle. In the illustrated example, the left ventricle issued as an estimate for the right ventricle because of the circular geometry of the left ventricle in the short-axis view.

$$p(X|Z) = \begin{cases} P_{LV}(X|Z) \propto p(Z|X)p_{LV}(X) \\ P_{RV}(X|Z) \propto p(Z|X)p_{RV}(X) \end{cases} \qquad \text{Equation 2}$$

In the illustrated example, based on the example Bayesian equation as described in Equation 2, an object state can be defined as $X=[X_1, \ldots X_Q]$ where $X_q \in \{0, 1\}$ is a label assigned to the qth pixel in the input image and $q \in \{1, \ldots, Q\}$ and where $\{0, 1\}$ corresponds to a background, the left ventricle and the right ventricle, respectively. In this example, X labels and partitions the image into the cavity and the background (e.g., into two segments). To determine an area of the cavity, in some examples, the posterior probability of the object state, X, is estimated using an example Bayesian inference method and the cavity area is determined based on a function of X. Using an estimation of the posterior probability, p(X|Z), Equation 3 can be used to determine the mean cavity area of the left ventricle and the right ventricle as a function of the posterior where $A(X)=\Sigma_q \delta(X_q, 1)$ and $\delta(a, b)$ is a Kronecker delta function. In the examples disclosed herein, A(X) determines the left ventricle cavity area and the right ventricle cavity area by counting the pixels labeled as 1.

$$\epsilon[A(X)|Z] = \Sigma_{X \in \{0,1\}} QA(X)p(X|Z) \qquad \text{Equation 3}$$

Equation 4 describes a likelihood function, p(Z|X), that uses a blob based appearance model, $p_b(Z|X)$, a homogeneity based appearance model, $p_h(Z|X)$, and an edge based appearance model, $p_e(Z|X)$ where $\alpha$ and $\beta$ are used to adjust the relative importance of each of the models. In the illustrated examples, the blob, homogeneity and edge based appearance models are assumed to be conditionally independent of each other given an object state, X, which is an assumption for integrating multiple features and/or models.

$$p(Z|X) = p_b(Z|X)p_h(Z|X)^\alpha p_e(Z|X)^\beta \qquad \text{Equation 4}$$

Figure 6:
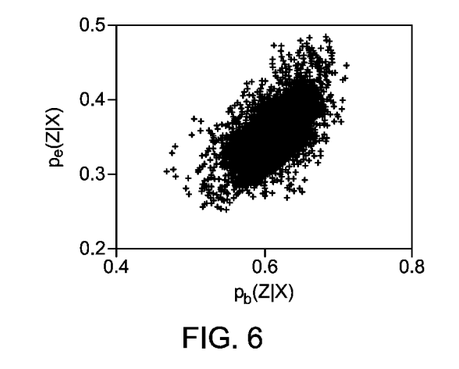
FIG. 6 shows a plot of an example blob based appearance model.
Figure 7:
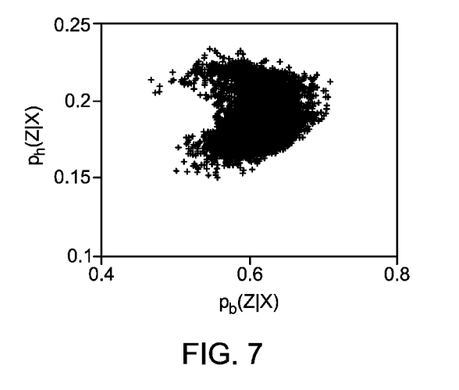
FIG. 7 shows a plot of an example homogeneity based appearance model.
Figure 8:
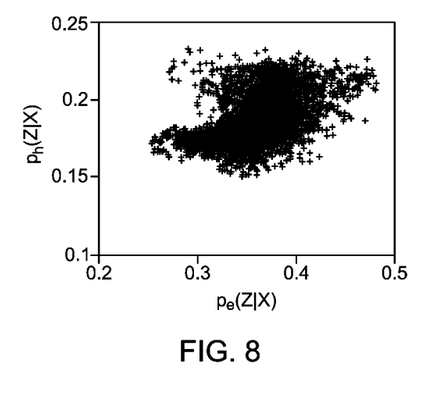
FIG. 8 shows a plot of an example edge based appearance model.

FIGS. 6, 7 and 8 show plots of the blob based appearance model, the homogeneity based appearance model and the edge based appearance model, respectively, based on an input image and hypothesized object states (e.g., approximately 3300) collected from manual segmenting data. A comparison between the blob based appearance model of FIG. 6 and the edge based appearance model of FIG. 8 shows a low degree of correlation. In some examples, the blob based appearance model is useful in medical imaging when objects have a blob-like appearance (e.g., an inside area is brighter or darker than a surrounding area). Because in an MRI, the left ventricle cavity and the right ventricle cavity may be brighter than neighboring structures, the blob based appearance model is advantageous when extracting cavity regions.

Figure 9:
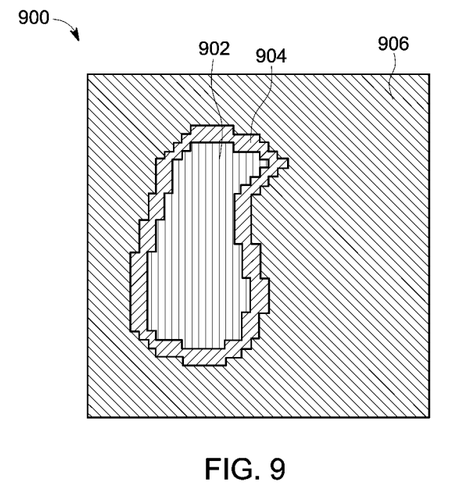
FIG. 9 is an example blob mask associated with a blob based appearance model.

FIG. 9 is associated with a blob based appearance model and illustrates an example mask 900 that captures blob features by determining the dot product with an input image. In the illustrated example of FIG. 9, fb(X) is the mask 900 constructed based on the object state, X, and fb q (X) is the qth pixel in the mask. As shown in FIG. 9, the mask 900 includes a cavity region (e.g., a white region) 902, a narrow band region (e.g., a black band or region) 904 and remaining and/or surrounding pixels (e.g., a grey region) 906. In the illustrated example, the pixel weight of the cavity region 902 is approximately 1, the pixel weight of the narrow band region 904 is approximately −1 and the pixel weight of the remaining pixels is approximately 0. Equation 5 describes a process of constructing the mask 900 of FIG. 9, where d is the width of the band, A(X) is the area of the left ventricle and the right ventricle, $\Omega_c(X)$ and $\Omega_b(X)$ are the cavity region 902 and the surrounding narrow band region 904. In the illustrated examples, the cavity region 902 and the surrounding narrow band region 904 are determined by the object state, X, and $\delta(\bullet)$ $$f_q^b(X) = \begin{cases} 1/A(X) & q \in \Omega_c(X) \\ -1 / \left\{ d * \sum_{k \in \{1, \ldots, Q\}} (1 - \delta(\nabla X_k)) \right\} & q \in \Omega_b(X) d* \\ 0 & \text{elsewhere} \end{cases}$$ Equation 5

Figure 10:
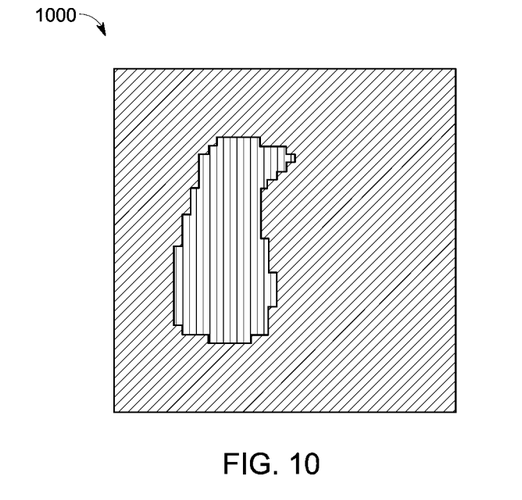
FIG. 10 illustrates an example homogeneity mask associated with a homogeneity based appearance model.

FIG. 10 illustrates an example homogeneity mask 1000 used to specify a cavity region within which homogeneity is computed. When the left ventricle and the right ventricle are filled with blood, except for a papillary muscle region, the left ventricle and the right ventricle may have a bright and homogeneous appearance in an MRI. The papillary muscle region provides for a homogeneity constraint in the object state, X (e.g., having low intensity variance in a specified cavity region). Even with possible disturbances from papillary muscles, homogeneity can provide for a complementary constraint for cavity estimation problems. Equation 6 is an example appearance model that captures the homogeneity feature, where $\mu(Z, X)$ is a mean intensity with the cavity region, $\Omega_C(X)$, specified by the object state, X, as shown in the example mask 1000 of FIG. 10. Equation 7 defines a mean intensity within the cavity region, $\Omega_C(X)$, specified by the object state, X.

$$p_h(Z|X) = 1 - \Sigma_{q \in \Omega} C_{(x)} (z_q - \mu(Z,X))^2 / A(X)$$ Equation 6

$$\mu(Z,X) = \Sigma_{z \in \Omega} C_{(x)} Z_q / A(X)$$ Equation 7

Figure 11:
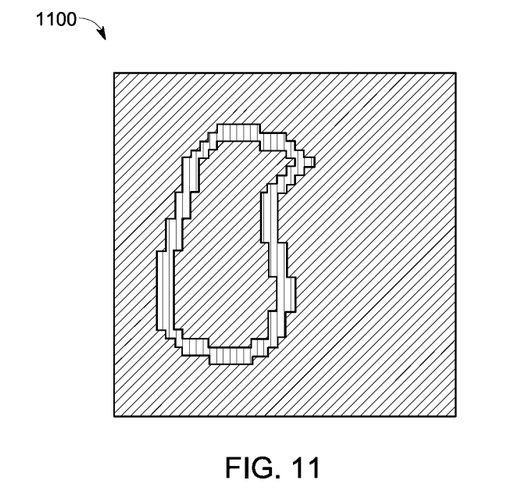
FIG. 11 shows an example edge mask associated with an example edge based appearance model.

FIG. 11 shows an example edge mask 1100 used to capture edge features by determining the dot product with an edge image. Edge features may be used in active contour based segmentation because edge features popularly exist and are efficiently computable. In the illustrated examples, edge features are used in both spatial and temporal domains. Edges in the spatial domain may correspond to high gradients along boundaries between the cavity and the myocardium. Edges in the temporal domain may correspond to motion of the cavity boundary during diastolic and systolic periods. Equation 8 is an example edge based appearance model where $f_e(X)$ represents the edge mask 1100 constructed based on Z and $f_q^e(X)$ is the qth pixel in the mask 1100. Equation 9 shows a formal construction of the mask 1100 where $\Omega_e(X)$ is the boundary of the cavity determined by the object state, X. In this example, an edge image, $Z^e$, is defined by Equation 10, where $\delta_r Z$, $\delta_c Z$ and $\delta_t Z$ are the first derivative in the row, column and temporal directions, respectively.

$$p_e(Z|X) = \langle Z^e, f^e(X) \rangle = \sum_{x \in \{1, \ldots Q\}} Z_q^e * f_q^e(X)$$ Equation 8

$$f_q^e(X) = \begin{cases} 1 / \sum_{k \in \{1, \ldots Q\}} 1 - \delta(\nabla X_k)) & q \in \Omega_e(X) \\ 0 & \text{elsewhere} \end{cases}$$ Equation 9

$$Z^e = \sqrt{(\delta_r Z)^2 + (\delta_c Z)^2} + |\delta_t Z|$$ Equation 10

In the illustrated examples, an example prior probability model uses joint information between the left ventricle and the right ventricle that results from motion similarity. Equation 11 shows how the joint information between the left ventricle and the right ventricle can be expressed as a linear correlation between the cavity areas where $A_R(t)$ and $A_L(t)$, respectively, represent the cavity areas of the right and left ventricles at a certain time, $t \in \{1, \ldots, T\}$, during a cardiac cycle of T frames, and $N(0, \sigma)$ represents Gaussian noise. The correlation between the left ventricle area and the right ventricle area, as shown in Equation 11, has been confirmed by manually segmented cavities in a dataset.

$$A_R(t) = \alpha^* A_L(t) + b + N(0, \sigma)$$ Equation 11

In the illustrated examples, the estimated area of the left ventricle cavity over a cardiac cycle obtained using Equation 11 can be used to predict the right ventricle area over the same cycle (e.g., a first prior or first right ventricle cavity area estimation). The first prior can be used to obtain a more accurate right ventricle posterior probability estimation. Equation 12 shows an example prior probability model that can be used to formulate and/or use the first prior by correlating the prior term, $f_{L \oplus R}(X, a, b, t)$, where $p_S X$ is an underlying prior distribution embedded in a training set and $f_{L \oplus R}(X, a, b, t)$ is determined and/or derived using Equation 13.

$$p_{RV}(X) = p(X \mid a, b, t) = f_{L \oplus R}(X, A, b, t) * p_s(X)$$ Equation 12

$$f_{L \oplus R}(X, a, b, t) = \frac{1}{\sqrt{2\pi}\sigma} \exp\left(-\frac{(aA_L(t) + b - (A(X))^2}{2\sigma^2}\right)$$ Equation 13

Referring to Equation 13, the parameter, t, indicates the frame index of the current object state, X, during a cardiac circle. Thus, a current right ventricle cavity area, A(X) or $A_R(t)$ of Equation 11, is linearly correlated to the left ventricle cavity area, $(A_L(t))$, in the same frame.

The example prior probability model of Equation 12 is configured to determine the right ventricle area using the corresponding left ventricle area information. For the left ventricle area information, the prior probability model uses the underlying distribution embedded in the training set described in Equation 14.

$$P_{LV}(X) = p_S(X)$$ Equation 14

Equation 15 shows a maximum posterior estimation (MAP) method for estimating the parameters, a, b, given all the images (e.g., an MRI sequence) during a cardiac cycle.

$$[\hat{a}, \hat{b}]_{MAP} = \arg\max_{[a,b]} p(a, b | Z_{1:T})$$ Equation 15

Equations 16-19 are processes to determine a posterior distribution, $p(a, b | Z_{1:T})$, in which the prior distribution of [a, b] is assumed to be uniform, $p(Z_{1:T})$ and constant, and equations 3 and 11 are defined in $p(Z_t | X_t)$ and $p(X_t | a, b) = p(X | a, b, t)$. When determining Equations 16-19, the following assumptions may be made including that the observation image at time, t, $Z_t$ is independent given the object state at the time, t, $Z_t$ and $X_t$ is independent provided the parameters a and b.

$$p(a, b | Z_{1:T}) = \sum_{X_1} \ldots \sum_{X_T} p(a, b, X_1 \ldots X_T | Z_{1:T})$$ Equation 16

$$= \sum_{X_1} \ldots \sum_{X_T} p(Z_{1:T}, X_1, \ldots, X_T, a, b) / p(Z_{1:T})$$ Equation 17

$$= \sum_{X_1} \ldots$$
$$\sum_{X_T} \{p(Z_{1:T}, X_1, \ldots, X_T, a, b) p(X_1, \ldots, X_T, a, b)\} /$$
$$p(Z_{1:T})$$ Equation 18

$$\sum_{X_1} \ldots \sum_{X_T} \{p(Z_1 | X_1) \ldots p(Z_T | X_T)$$
$$p(X_1 | a, b) \ldots p(X_T | a, b) p(a, b)\} / p(Z_{1:T})$$ Equation 19

To determine the cavity area of the right ventricle and the left ventricle, a sample set, $\{S_1, \ldots, S_N\}$, is created from a training set in which, during a training phase, each input image is manually segmented into the left ventricle, the right ventricle and the background. In the illustrated example, the training set is produced using Equation 20 in which all left ventricle and right ventricle images are collected together to naturally embed different prior information about the shape, location and scale in the training set.

$$P_S(X) \approx \Sigma_{i=1}^N \delta(X,s_i)/N \qquad \text{Equation 20}$$

$$\epsilon[A(X)|Z] \approx \Sigma_{i=1}^N A(s_i)\pi_i \qquad \text{Equation 21}$$

To incorporate additional priors and/or information into the training set, in the illustrated examples, the sample weight may be modified to include prior terms such as the mutual information term, $f_{L \oplus R}(X, a, b, t)$, determined using Equation 12 and/or by computing the sample weight as a product of $f_{L \oplus R}(X, a, b, t)$ and the example likelihood function, $p(Z|X)$ and/or other correlation information between the left ventricle and the right ventricle.

In some examples, each sample within the sample set is assigned a weight, $\pi_i$, based on the likelihood function described in Equation 4 where the weighting for the left ventricle is described in Equation 22 and the weighting for the right ventricle is described in Equation 23. Equation 24 is used to normalize the weighted sample set, $\{S_i, \pi_i\}_{i=1}^N$, which can be used to approximate the posterior density, $p(X|Z)$. Equation 21 can be used to estimate the cavity area, $\epsilon[A(X)|Z]$.

$$\pi_i = p(Z_t|X=s_i) \qquad \text{Equation 22}$$

$$\pi_i = p(Z_t|X=s_i) * f_{L \oplus R}(X,a,b,t) \qquad \text{Equation 23}$$

$$\{\pi_i\}_{i=1}^N \text{ to } \{\tilde{\pi}_i\}_{i=1}^N \qquad \text{Equation 24}$$

In the illustrated examples, to determine the ventricular volumes of the left ventricle and the right ventricle, the cavity areas are integrated in short-axis view slices along a sagittal direction by summing the volume of each slice. Equation 25 can be used to determine the volume of the ventricles by summing the product of the corresponding cavity area, $A_i$, and slice thickness, h.

$$V = \Sigma_i A_i * h \qquad \text{Equation 25}$$

Figure 12:
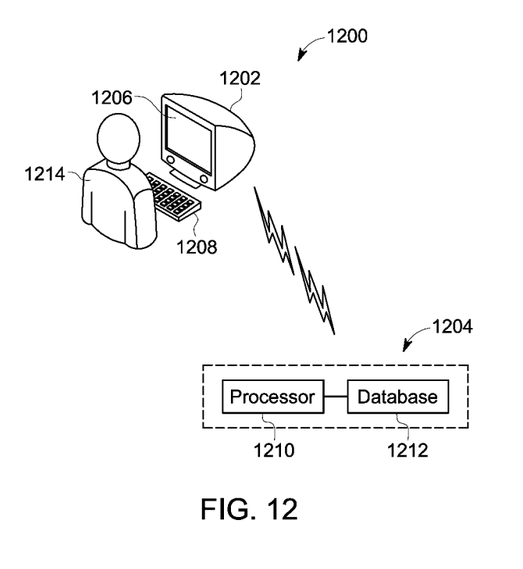
FIG. 12 shows an example system in accordance with the examples disclosed herein.

FIG. 12 depicts an example system 1200 for estimating (e.g., automatically estimating) ventricular volumes. In some examples, the system 1200 includes a computer 1202 and a generator 1204 communicatively coupled to the computer 1202. In this example, the computer 1202 includes a user interface 1206 and a data input (e.g., a keyboard, mouse, microphone, etc.) 1208 and the generator 1204 includes a processor 1210 and a database or other data store 1212.

In some examples, the user interface 1206 displays data such as images (e.g., MRI sequence, frames, etc.) received from the generator 1204. In some examples, the user interface 1206 receives commands and/or input from a user 1214 via the data input 1208. For example, in examples in which the system 1020 is used to determine the areas and/or volumes of the left ventricle or the right ventricle, the user interface 1206 displays a frame(s) of cardiac MRI images in a short-axis view and the user 1214 provides an initial input identifying, for example, a location(s) on a basal slice of the intersection between the left ventricular septal wall and a right ventricular wall. In the illustrated example, the initial input includes selecting two points on the frame.

In other examples, the initial input may be performed automatically. In some such examples, a region of interest (e.g., a course ROI) may be identified and/or extracted by identifying moving parts in the MRI sequence and/or scene (e.g., the left ventricle and the right ventricle move significantly during a cardiac cycle). In some examples, the ROI includes fitting a bounding box over and/or to a region having high intensity variance over a cardiac cycle. In some example, within the region of interest, the left ventricle can be detected and/or identified using a Hough circle transform and the right ventricle may be detected and/or identified by template matching the regions geometrically constrained by the detected left ventricle. After the right ventricle is identified, the initial input of the intersections between the left and right ventricles are identified (e.g., automatically identified) by mapping two corresponding landmarks of a template in an original image coordinate.

In the illustrated example, based on the initial input, the processor 1210 automatically identifies and extracts a region of interest in each slice and/or frame of the MRI sequence that includes and/or encompasses both the left ventricle and the right ventricle. In the illustrated examples, the processor 1210 automatically determines the area(s) of the right ventricle and the left ventricle by generating a sample set using an example prior probability model for the right and left ventricles and assigning a weight to each sample within the set based on an example likelihood function. Additionally, in the illustrated examples, to determine the area(s) of the right ventricle and the left ventricle, the weighted sample set is normalized and then used to approximate the posterior density and the area of the left ventricle and right ventricle. In the illustrated examples, the processor 1210 automatically determines the volume(s) of the right ventricle and left ventricle by summing the volume of each slice (e.g., product of the cavity area (Ai) and the slice thickness (h).

In the illustrated examples, using determined area(s) and/or volume(s) and/or other information stored in the data 1212, the processor 1210 may generate a figure and/or chart to assist in assessing cardiac functionality. These generated figures and/or charts can be displayed at the user interface 1206. In the illustrated examples, using the determined area(s) and/or volume(s) and/or other information stored in the data 1212, the processor 1210 may generate and cause the display of an overlay of the identified left ventricle and the right ventricle over the corresponding MRI sequence and/or one or more frames of the MRI sequence to enable visual validation. In the illustrated examples, using the determined area(s) and/or volume(s) and/or other information stored in the data 1212, the processor 1210 may automatically insert into and/or generate a report using functional parameters as disclosed herein.

Figure 13:
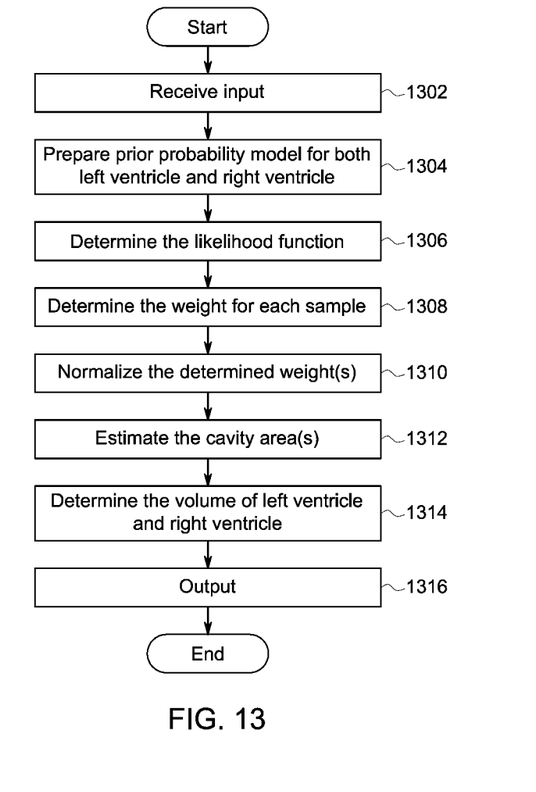
FIG. 13 is a flowchart representative of machine readable instructions that may be executed to implement the system of FIG. 12.

While an example manner of implementing the system 1200 of FIG. 12 is illustrated in FIG. 13, one or more of the elements, processes and/or devices illustrated in FIG. 13 may be combined, divided, re-arranged, omitted, eliminated and/or implemented in any other way. Further, the computer 1202, the generator 1204, the user interface 1206 the data input 1208 and/or, more generally, the example system 1200 of FIG. 12 may be implemented by hardware, software, firmware and/or any combination of hardware, software and/or firmware. Thus, for example, any of the example, the computer 1202, the generator 1204, the user interface 1206, the data input 1208 and/or, more generally, the example system 1200 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example, the computer 1202, the generator 1204, the user interface 1206, the data input 1208 and/or, more generally, the example system 1200 is/are hereby expressly defined to include a tangible computer readable storage device or storage disk such as a memory, a digital versatile disk (DVD), a compact disk (CD), a Blu-ray disk, etc. storing the software and/or firmware. Further still, the example system of FIG. 12 may include one or more elements, processes and/or devices in addition to, or instead of, those illustrated in FIG. 13, and/or may include more than one of any or all of the illustrated elements, processes and devices.

A flowchart representative of example machine readable instructions for implementing the example system 13 is shown in FIG. 13. In this example, the machine readable instructions comprise a program for execution by a processor such as the processor 1612 shown in the example processor platform 1600 discussed below in connection with FIG. 16. The program may be embodied in software stored on a tangible computer readable storage medium such as a CD-ROM, a floppy disk, a hard drive, a digital versatile disk (DVD), a Blu-ray disk, or a memory associated with the processor 1612, but the entire program and/or parts thereof could alternatively be executed by a device other than the processor 1612 and/or embodied in firmware or dedicated hardware. Further, although the example program is described with reference to the flowchart illustrated in FIG. 16, many other methods of implementing the example system 1600 may alternatively be used. For example, the order of execution of the blocks may be changed, and/or some of the blocks described may be changed, eliminated, or combined.

As mentioned above, the example processes of FIG. 12 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIG. 12 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term "non-transitory computer readable medium" is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

Figure 14:
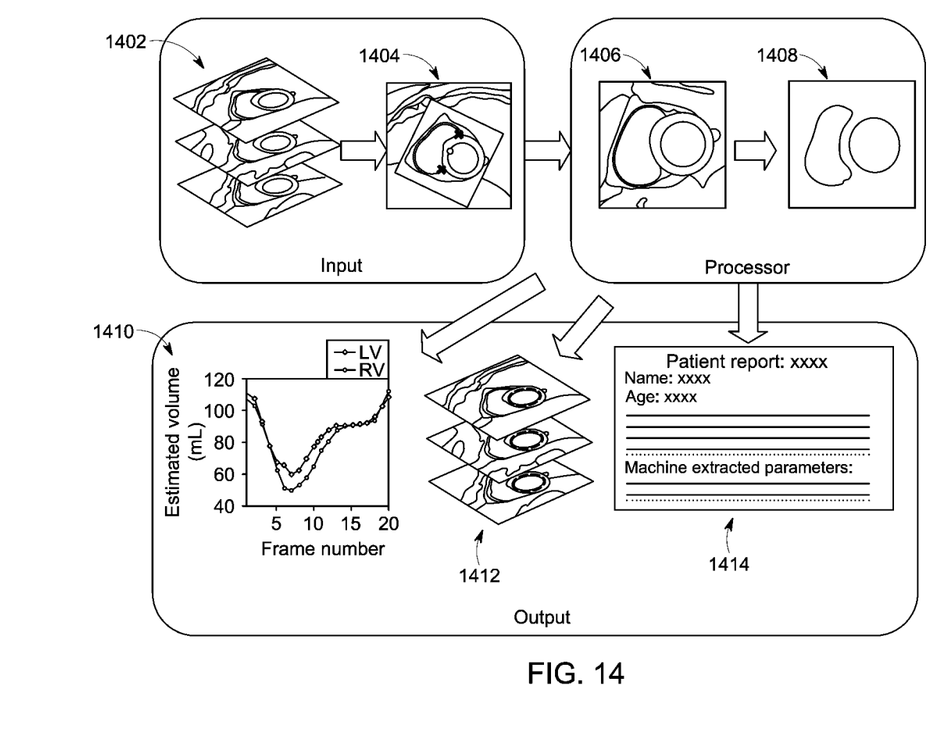
FIG. 14 is a flow diagram illustrating some of the processes described in the flowchart of FIG. 13.

With reference to FIGS. 13 and 14, the program of FIG. 13 begins at block 1300 where the user interface 1206 receives commands and/or input from a user 1214 via the data input 1208 (block 1302). For example, the user interface 1206 displays a frame(s) of a cardiac MRI image(s) (in a short-axis view) (1402 of FIG. 14) and the user 1214 provides an initial input identifying, for example, a location(s) on a basal slice of the intersection between the left ventricular septal wall and a right ventricular wall (1404 of FIG. 14). In the illustrated example, the initial input includes selecting two points on the frame. In other examples, the initial input may be performed automatically. Based on the initial input, a region of interest (ROI) (1406 of FIG. 14) is automatically identified and/or extracted that encloses both the left ventricle and the right ventricle.

In the illustrated example, the bi-ventricular regions are automatically estimated using the examples disclosed herein (1408 FIG. 14). Specifically, the processor 1210 automatically determines the area(s) of the right ventricle and the left ventricle by generating a sample set using an example prior probability model for the right and left ventricles. (block 1304). The program then determines a likelihood function (block 1306). Using the likelihood function, a weight is assigned to each sample within the set (block 1308). At block 1310, the sample set is normalized (block 1310). In the illustrated examples, the normalized sample set is used to approximate posterior density, which is used to determine the area of the left ventricle and the right ventricle and/or the area of the cavities (block 1312). In the illustrated examples, the processor 1210 automatically determines the volume(s) of the right ventricle and the left ventricle by summing the volume of each slice (e.g., product of the cavity area (Ai) and the slice thickness (h) (block 1314). At block 1316, the program generates an output (block 1314). In the illustrated examples, the output may include displaying figures and/or charts on a user display to assist in cardiac functional assessment (1410 of FIG. 14). In the illustrated examples, the output may include displaying an MRI with a visual marker overlaid on a user display for manual validation (1412 of FIG. 14). In the illustrated examples, the output may include automatically inserting machine extracted functional parameters into a patient report (1414 of FIG. 14).

Figure 15:
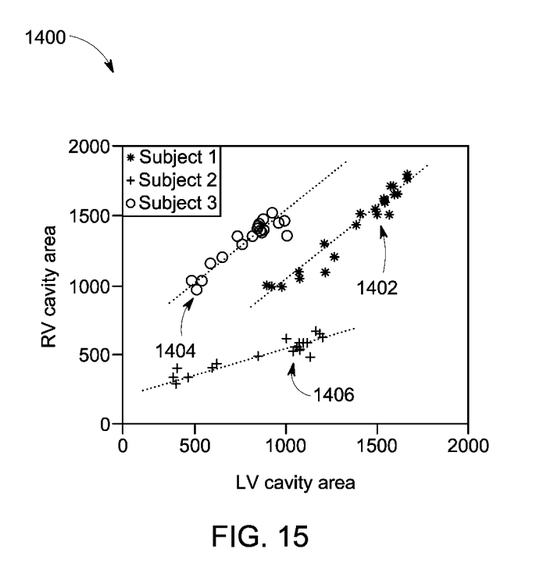
FIG. 15 is a graph showing the correlation between the left ventricle cavity area and the right ventricle cavity area.

FIG. 15 shows an example plot 1500 of left ventricular area and the right ventricular area of a first subject and/or individual 1502, a second subject and/or individual 1504 and a third subject and/or individual 1506. The plots lying in a straight line demonstrate the linear correlation between right ventricular area at a time, $A\_R$ (t) and the left ventricular area at the time $A\_L$ (t) with different slopes ($\alpha$) and RV-axis intercept (b).

Figure 16:
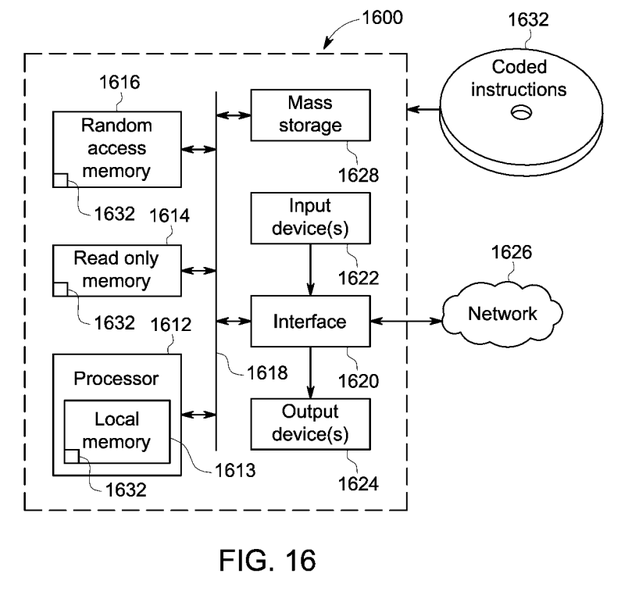
FIG. 16 is a processor platform to execute the instructions of FIG. 13 to implement the system of FIG. 12.

FIG. 16 is a block diagram of an example processor platform 1000 capable of executing the instructions of FIG. 13 to implement the system 1200 of FIG. 12. The processor platform 1600 can be, for example, a server, a personal computer, a mobile device (e.g., a cell phone, a smart phone, a tablet such as an IPAD™), a personal digital assistant (PDA), an Internet appliance, or any other type of computing device.

The processor platform 1600 of the illustrated example includes a processor 1652. The processor 1612 of the illustrated example is hardware. For example, the processor 1612 can be implemented by one or more integrated circuits, logic circuits, microprocessors or controllers from any desired family or manufacturer.

The processor 1612 of the illustrated example includes a local memory 1613 (e.g., a cache). The processor 1612 of the illustrated example is in communication with a main memory including a volatile memory 1614 and a non-volatile memory 1616 via a bus 1618. The volatile memory 1614 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1616 may be implemented by flash memory and/or any other desired type of memory device. Access to the main memory 1614, 1616 is controlled by a memory controller.

The processor platform 1600 of the illustrated example also includes an interface circuit 1020. The interface circuit 1620 may be implemented by any type of interface standard, such as an Ethernet interface, a universal serial bus (USB), and/or a PCI express interface.

In the illustrated example, one or more input devices 1622 are connected to the interface circuit 1620. The input device(s) 1622 permit(s) a user to enter data and commands into the processor 1612. The input device(s) can be implemented by, for example, a keyboard, a button, a mouse, a touchscreen, a track-pad, a trackball, isopoint and/or a voice recognition system.

One or more output devices 1624 are also connected to the interface circuit 1620 of the illustrated example. The output devices 1624 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED)). The interface circuit 1620 of the illustrated example, thus, typically includes a graphics driver card, a graphics driver chip or a graphics driver processor.

The interface circuit 1620 of the illustrated example also includes a communication device such as a transmitter, a receiver, a transceiver, a modem and/or network interface card to facilitate exchange of data with external machines (e.g., computing devices of any kind) via a network 1626 (e.g., an Ethernet connection, a digital subscriber line (DSL), a telephone line, coaxial cable, a cellular telephone system, etc.).

The processor platform 1600 of the illustrated example also includes one or more mass storage devices 1628 for storing software and/or data. Examples of such mass storage devices 1028 include floppy disk drives, hard drive disks, compact disk drives, Blu-ray disk drives, RAID systems, and digital versatile disk (DVD) drives.

The coded instructions 1632 of FIG. 13 may be stored in the mass storage device 1328, in the volatile memory 1314, in the non-volatile memory 1316, and/or on a removable tangible computer readable storage medium such as a CD or DVD.

From the foregoing, it will appreciate that the above disclosed methods, apparatus and articles of manufacture enable automated right ventricle functional assessments, processing of the left and right ventricles substantially simultaneously and/or simultaneously and/or the direct performance of inter-ventricular analysis and/or regurgitant valvular disease detection.

The disclosed examples enable enhanced usability with little if any human interaction (e.g., two manual clicks) to perform bi-ventricular functional assessments. The disclosed examples enable improved efficiencies by removing tedious human interactions and inefficient segmentation steps, thereby providing real-time functional assessment tools and/or processing-time efficiencies. The disclosed examples provide advanced functionalities including an automated too for bi-ventricular functional assessment, comprehensive parameter estimation in each frame (e.g., instead of just end-systolic and end-diastolic frames) and/or direct inter-ventricular analysis by jointly investigating the bi-ventricular parameters (e.g., diagnosis of regurgitant valvular disease or intra-cardiac shunts, etc.).

The examples disclosed herein relate to an example method for estimating the volume of both the left ventricle and the right ventricle jointly without segmentation, an example likelihood function that uses multiple appearance features and/or an example probability model that uses area correlation information.

Methods and apparatus to estimate Cardiac biventricular volumes jointly are disclosed. An example computer-implemented method includes preparing a sample set, computing a prior probability model for a left ventricle and a right ventricle and using a likelihood function to assign a weight to each sample within the sample set. The example method includes, based on the weighted sample set, determining a cavity area of the right ventricle and the left ventricle in a slice. The example method includes integrating the determined areas over slices covering the whole heart to obtain the biventricular volumes.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A computer-implemented method, comprising:
   accessing data relating to a first attachment point between a left ventricle and a right ventricle and a second attachment point between the left ventricle and the right ventricle;
   based on the data, preparing a sample set using a prior probability model for the left ventricle and the right ventricle;
   using a likelihood function to assign a weight to each sample within the sample set; and
   based on the weighted sample set, determining a bi-ventricular area of the right ventricle and the left ventricle.

2. The method of claim 1, wherein the area includes a first area associated with the left ventricle and a second area associated with the right ventricle.

3. The method of claim 1, further including, based on the area of the left ventricle and the right ventricle, determining a volume of the left ventricle and the right ventricle.

4. The method of claim 1, wherein the sample set is associated with a plurality of frames of a magnetic resonance imaging (MRI) series.

5. The method of claim 1, further including automatically generating a medical report in which the determined bi-ventricular area is included.

6. The method of claim 1, further including generating a representation of the left ventricle and the right ventricle based on the area.

7. The method of claim 1, wherein the prior probability model uses correlating information between the left ventricle and the right ventricle.

8. The method of claim 1, wherein the determining of the bi-ventricular area of the right ventricle and the left ventricle includes a segmentation-free process of using a Bayesian formulation.

9. The method of claim 1, further including, prior to the determining of the bi-ventricular area of the right ventricle and the left ventricle, orientating a region of interest based on a line intersecting the first attachment point and the second attachment point, the region of interest including the right ventricle and the left ventricle.

10. The method of claim 9, wherein the orientating of the region of interest includes orientating the region of interest to enable the line to be vertically disposed.

11. A method, comprising:
- accessing an input associated with an image including a left ventricle and a right ventricle, the input including a first landmark of the left ventricle and a second landmark of the right ventricle;
- based on the input, automatically identifying a region of interest on the image;
- using the region of interest, preparing a sample set using a prior probability model for the left ventricle and the right ventricle;
- using a likelihood function to assign a weight to each sample within the sample set; and
- based on the weighted sample set, determining a bi-ventricular area of the left ventricle and the right ventricle.

12. The method of claim 11, wherein the first landmark corresponds to a first intersection between the left ventricle and the right ventricle and the second landmark corresponds to a second intersection between the left ventricle and the right ventricle, the first and second intersections are automatically identified.

13. The method of claim 12, wherein the first intersection and the second intersection are automatically identified by automatically identifying the left ventricle and the right ventricle based on movement of the left ventricle and the right ventricle in a plurality of frames of a magnetic resonance imaging (MRI) series.

14. The method of claim 11, wherein the first landmark and the second landmark are received from a user input.

15. The method of claim 11, wherein the area includes a first area associated with the left ventricle and a second area associated with the right ventricle.

16. The method of claim 11, further including, based on the area of the left ventricle and the right ventricle, determining a volume of the left ventricle and the right ventricle.

17. The method of claim 11, wherein the sample set is associated with a plurality of frames of a magnetic resonance imaging (MRI) series.

18. A system, comprising:
- a processor, wherein in response to receiving a first input including a first landmark of a left ventricle and a second landmark of a right ventricle, the processor to automatically identify a region of interest on an image including the left ventricle and the right ventricle, based on the region of interest, the processor to generate a sample set using a prior probability model for the left ventricle and the right ventricle, the processor to determine and use a likelihood function to assign a weight to each sample within the sample set, the processor to determine a bi-ventricular area of the left ventricle and the right ventricle based on the weighted sample set.

19. The system of claim 18, further including a data store in which the determined area is stored.

20. The system of claim 18, wherein the processor is to further determine a volume of the left ventricle and the right ventricle based on the determined area.

21. The system of claim 18, wherein the area includes a first area associated with the left ventricle and a second area associated with the right ventricle.

22. The system of claim 18, wherein the processor is to further generate a representation of the left ventricle and the right ventricle based on the area.

* * * * *